(12) United States Patent
Qin et al.

(10) Patent No.: US 12,428,616 B2
(45) Date of Patent: *Sep. 30, 2025

(54) CONJUGATION DEVICE AND METHOD FOR PRODUCING CONJUGATES

(71) Applicants: GENEQUANTUM HEALTHCARE (SUZHOU) CO., LTD., Suzhou (CN); LISURE SCIENCE (SUZHOU) CO., LTD, Suzhou (CN)

(72) Inventors: Gang Qin, Suzhou (CN); Sheng Zhou, Suzhou (CN); Cao Lv, Suzhou (CN); Joachim Walter, Mittelbiberach (DE)

(73) Assignees: GENEQUANTUM HEALTHCARE (SUZHOU) CO., LTD., Suzhou (CN); LISURE SCIENCE (SUZHOU) CO., LTD, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,225

(22) Filed: May 7, 2024

(65) Prior Publication Data

US 2024/0287432 A1    Aug. 29, 2024

Related U.S. Application Data

(63) Continuation of application No. 18/150,632, filed on Jan. 5, 2023, now Pat. No. 12,012,582, which is a
(Continued)

(51) Int. Cl.
*C12M 1/00* (2006.01)
*C12M 1/02* (2006.01)

(52) U.S. Cl.
CPC ............ *C12M 29/18* (2013.01); *C12M 27/00* (2013.01); *C12M 29/16* (2013.01); *C12M 29/26* (2013.01)

(58) Field of Classification Search
CPC ...... C12M 29/18; C12M 29/16; C12M 29/26; C12M 27/00; C12M 21/18;
(Continued)

(56) References Cited

U.S. PATENT DOCUMENTS

| 4,158,609 A | 6/1979 | Muller |
| 5,352,585 A | 10/1994 | Binder et al. |

(Continued)

FOREIGN PATENT DOCUMENTS

| CN | 204789498 U | 11/2015 |
| CN | 106290592 A | 1/2017 |
| CN | 210690498 U | 6/2020 |

OTHER PUBLICATIONS

Beerli, et al., "Sortase Enzyme-Mediated Generation of Site-Specifically Conjugated Antibody Drug Conjugates with High In Vitro and In Vivo Potency", *PLOS One*, vol. 10, No. 7, pp. e0131177, (2015).
(Continued)

*Primary Examiner* — Michael L Hobbs
(74) *Attorney, Agent, or Firm* — Hoxie & Associates LLC (57) ABSTRACT

A conjugation device includes at least one flow reactor having an inlet and an outlet, the flow reactor(s) being completely filled with a support such as a matrix including 1) chromatography beads, fibers or membranes, and 2) a biologic catalyzer, namely the enzyme ligase, which is immobilized onto this support; a fluid delivery unit in fluid communication with the inlet of the flow reactor(s) and configured to continuously provide the flow reactor(s) with at least one kind of reaction fluid such as antibody and linker-payload according to stages of the conjugation process, the at least one kind of process fluid including a first moiety and a second moiety of a conjugate to be produced; and a fluid collection unit in fluid communication with the outlet of the flow reactor(s) and configured to control
(Continued)

collection of fluid flowing out of the outlet of the flow reactor(s) according to the stages of the conjugation process. In a period of enabling the at least one kind of reaction fluid to continuously flow through the flow reactor(s), a conjugation reaction is conducted between the first moiety and the second moiety under catalysis of the ligase to produce the conjugate.

19 Claims, 5 Drawing Sheets

Related U.S. Application Data continuation of application No. 17/667,705, filed on Feb. 9, 2022, now Pat. No. 11,578,297.

(58) Field of Classification Search
CPC ....... C12Y 304/2207; C12Y 304/22071; C12P 19/04; C12P 19/34; C12P 21/02; C12Q 1/34; C12Q 1/37; B01J 9/0046; B01J 9/245; B01J 8/0278; B01J 31/003; B01J 2219/00337; B01J 2219/00353; B01J 2219/0072
See application file for complete search history.

(56) References Cited

U.S. PATENT DOCUMENTS

| | | | |
|---|---|---|---|
| 6,962,809 | B1 | 11/2005 | Deguchi et al. |
| 11,578,297 | B2 * | 2/2023 | Qin .......................... C12P 19/34 |
| 12,012,582 | B2 * | 6/2024 | Qin .......................... C12Q 1/34 |
| 2014/0235839 | A1 | 8/2014 | Yamaguchi |
| 2019/0177714 | A1 | 6/2019 | Kunze et al. |
| 2019/0194641 | A1 | 6/2019 | Spycher et al. |
| 2019/0270769 | A1 | 9/2019 | Milano et al. |
| 2020/0164338 | A1 | 5/2020 | Lingen et al. |
| 2020/0282376 | A1 * | 9/2020 | Asano ..................... B01F 35/71 |
| 2023/0159875 | A1 | 5/2023 | Qin et al. |

OTHER PUBLICATIONS

De Simone, A. et al., "Immobilized Enzyme Reactors: an Overview of Applications in Drug Discovery from 2008 to 2018", *Chromatographia*, vol. 82, No. 1, pp. 425-441, (2019).

Policarpo, R. et al., "Flow-Based Enzymatic Ligation by Sortase 1-19 A", *Angew. Chem. Int. Ed.*, vol. 53, pp. 9203-9208, (2014).

Witte, M. et al., "Site-specific protein modification using immobilized sortase in batch and continuous-flow systems", *Nat. Protoc.*, vol. 10, No. 3, pp. 508-516, (2015).

* cited by examiner

CONJUGATION DEVICE AND METHOD FOR PRODUCING CONJUGATES

CROSS REFERENCE TO RELATED APPLICATIONS

This application is a continuation of U.S. application Ser. No. 18/150,632, filed on Jan. 5, 2023, now U.S. Pat. No. 12,012,582, which is a continuation of U.S. Application Ser. No. 17/667,705, filed on Feb. 9, 2022, now U.S. Pat. No. 11,578,297, which claims the benefit of International Application Nos. PCT/CN2021/076218 filed on Feb. 9, 2021, and PCT/CN2021/087115 filed on Apr. 14, 2021, the contents of each of which are incorporated herein by reference.

FIELD OF THE DISCLOSURE

This disclosure relates generally to biotechnology and pharmaceutical production, more particularly, to a conjugation device and a method for producing conjugates by using the conjugation device.

BACKGROUND

Conjugation links one molecule to another via a specific linker by a biological or chemical method. Demands for high-quality conjugates, particularly bioconjugates, such as those for bioscience research, diagnosis or therapeutics purposes, are continuously increasing. The bioconjugates, such as antibody-drug conjugates (ADC), antibody-immune agonist conjugates, antibody-cytokine conjugates and antibody-nuclide conjugates, are formed by linking a targeting molecule with a payload via a linker.

Taking ADC as an example, major components of ADC include an antibody, a linker and a small-molecule compound. The antibody is mainly used to deliver the small-molecule compound to a specific target, and the small-molecule compound (including but not limit to cytotoxin) produces therapeutic effects on the target. At present, the nine ADC drugs approved by FDA are formed in a chemical conjugation manner, i.e., the cytotoxin is randomly conjugated onto lysine or cysteine residues of an antibody frame.

In the chemical conjugation manner, a monoclonal antibody stock solution needs to be produced by upstream and downstream processes which utilize raw materials of the antibody prior to a conjugation process. Thereafter, the following steps are performed in the conjugation process. The antibody is pretreated (e.g. chemically reduced), then the linkers are conjugated and dissociative linkers are removed by UF/DF and/or chromatography. After that, the small-molecule compounds are conjugated and aggregates are removed by cationic and/or anionic and/or hydrophobic chromatography. Finally, dissociative small-molecule compounds are removed by UF/DF and/or chromatography.

SUMMARY

Many problems exist in chemical conjugation, such as random conjugation sites, heterogeneous product, complex central control and restricted yield scale-up.

Firstly, a chemical conjugation product is generally a mixture of non-uniform structures and components. The conjugation between the linker and the antibody is highly random, which leads to diverse number of small-molecule compounds conjugating to the antibody and also diverse conjugation site of the antibody, and therefore the bioconjugates such as the ADC drugs may have different drug/antibody ratios (DAR). As a result, the bioconjugates exhibit high heterogeneity which results in great inter-batch differences and narrow therapeutic window and accordingly brings challenge to drug production as well as quality control.

Secondly, as described above, the production process of the chemical conjugation involves a significant number of steps, including multiple upstream and downstream purification steps, which is time-consuming and labor intensive.

Further, in some cases, the operator needs to conduct timed sampling during chemical conjugation and then DAR of the sample is calculated. The next operation will suspend until the calculation result is in line with an inner quality standard. Therefore, in these cases, the calculation of DAR is time-consuming, relatively costly, and the risk of a human error is increased.

In addition, a conventional reactor is generally used in chemical conjugation. The volume of the reactor restricts the potential to scale up. Also, an organic phase is required in the process of conjugation. Therefore, the conjugation process is difficult to be precisely controlled.

With respect to the above technical problems, a first aspect of the disclosure provides a conjugation device. Said conjugation device includes at least one flow reactor having an inlet and an outlet, the flow reactor(s) being completely filled with a support such as a matrix including chromatography beads, fibers or membranes, and a biologic catalyzer, namely the enzyme ligase, are immobilized onto the support; a fluid delivery unit in fluid communication with the inlet of the flow reactor(s) and configured to continuously provide the flow reactor(s) with at least one kind of reaction fluid (antibody, linker-toxin, mixed antibody and linker-toxin, etc.) according to stages of the conjugation process, the at least one kind of process fluid containing a first moiety and a second moiety of a conjugate to be produced; and a fluid collection unit in fluid communication with the outlet of the flow reactor(s) and configured to control collection of fluid flowing out of the outlet of the flow reactor(s) according to the stages of the conjugation process. In a period of enabling the at least one kind of reaction fluid to continuously flow through the flow reactor(s), a conjugation reaction is conducted between the first moiety and the second moiety under catalysis of the ligase to produce the conjugate.

In the conjugation device provided by the first aspect of the disclosure, the ligase is directionally immobilized onto the support and filled into the flow reactor, so that the two moieties of the conjugate to be produced contained in the reaction fluid are continuously and stably conjugated while the reaction fluid passes the fluid reactor. Compared with the chemical conjugation, the conjugation device greatly decreases the process steps, significantly reduces the complexity and is highly suitable to save expensive manufacturing costs. Moreover, by virtue of the flow reactor, linear scale-up of the conjugation process can be realized to satisfy industrial demands for larger scales, unit time for conjugation is shortened, and the occupied space in the manufacturing area is reduced. By producing the bioconjugates using the conjugation device, site-specific conjugation between payload-linker and targeting molecule is realized, the homogeneity is improved, and accordingly the therapeutic window is widened. In addition, the conjugation process can be integrated with production procedures of biomolecules such as monoclonal antibodies. For example, conjugation may be completed at stages of producing monoclonal antibody intermediates and monoclonal antibody stock solutions. Therefore, the process is high in flexibility and excellent in coherence.

In some embodiments, the at least one kind of reaction fluid includes first reaction fluid and second reaction fluid. The first reaction fluid contains the first moiety and the second reaction fluid contains the second moiety.

In some embodiments, the conjugation process sequentially includes the following stages: equilibrium prior to reaction, conjugation reaction, post-reaction, and flushing after post-reaction. Moreover, the fluid delivery unit is further configured to continuously provide the flow reactor(s) with a buffer solution during the stages of equilibrium prior to reaction, post-reaction and flushing after post-reaction and continuously and simultaneously provide the flow reactor(s) with the first reaction fluid and the second reaction fluid during conjugation reaction.

In some embodiments, the buffer solution, the first reaction fluid and the second reaction fluid are respectively stored in a first container, a second container and a third container. The fluid delivery unit includes a first delivery pump and a second delivery pump. The first container and the second container are connected to the first delivery pump via a first container outlet tube and a second container outlet tube; the third container is connected to the second delivery pump via a third container outlet tube; the first delivery pump and the second delivery pump are respectively connected to an inlet main tube via a first inlet branch tube and a second inlet branch tube, and the inlet main tube is connected to the inlet of the flow reactor. Moreover, during the stages of equilibrium prior to reaction, post-reaction and flushing after post-reaction, the buffer solution in the first container is pumped into the inlet main tube by the first delivery pump; and during the stage of conjugation reaction, the first reaction fluid in the second container is pumped into the inlet main tube by the first delivery pump, and the second reaction fluid in the third container is pumped into the inlet main tube by the second delivery pump.

In some embodiments, the fluid delivery unit further includes a first valve, a second valve, a third valve, and a fourth valve. The first valve, the second valve and the third valve are respectively arranged on the first container outlet tube, the second container outlet tube and the third container outlet tube and are respectively used for controlling flow path of fluid in the first container outlet tube, the second container outlet tube and the third container outlet tube; and the fourth valve is arranged on the first inlet branch tube and is used for controlling flow path of fluid in the first inlet branch tube.

In some embodiments, during the stages of equilibrium prior to reaction, post-reaction and flushing after post-reaction, the first valve and the fourth valve are opened, while the second valve and the third valve are closed; and during the stage of conjugation reaction, the first valve is closed, while the second valve, the third valve and the fourth valve are opened.

In some embodiments, the first container outlet tube, the second container outlet tube, the third container outlet tube, the first inlet branch tube, the second inlet branch tube and the inlet main tube are disposable or non-disposable and respectively made of one of stainless steel, titanium and silicone. The first container, the second container and the third container are respectively selected from one of disposable liquid storage bags, disposable liquid storage bottles, stainless steel containers, and both disposable and non-disposable glass or plastic containers.

In some embodiments, the fluid collection unit is further configured to collect fluid flowing out of the outlet of the flow reactor(s) into a fourth container during the stages of equilibrium prior to reaction and flushing after post-reaction, and collect fluid flowing out of the outlet of the flow reactor(s) into a fifth container during the stages of conjugation reaction and post-reaction.

In some embodiments, the fourth container and the fifth container are respectively connected to an outlet main tube connected to the outlet of each flow reactor via a fourth container inlet tube and a fifth container inlet tube. Moreover, the fluid collection unit includes a fifth valve and a sixth valve respectively arranged on the fourth container inlet tube and the fifth container inlet tube and used for controlling flow path of fluid in the fourth container inlet tube and the fifth container inlet tube.

In some embodiments, during the stages of equilibrium prior to reaction and flushing after post-reaction, the fifth valve is opened, while the sixth valve is closed; and during the stages of conjugation reaction and post-reaction, the fifth valve is closed, while the sixth valve is opened.

In some embodiments, the fourth container inlet tube and the fifth container inlet tube are disposable or non-disposable and respectively made of one of stainless steel, titanium and silicone. The fourth container and the fifth container are respectively selected from one of disposable liquid storage bags, disposable liquid storage bottles, stainless steel containers, and both disposable and non-disposable glass or plastic containers.

In some embodiments, the conjugation device further includes a temperature control unit configured to control a temperature of fluid flowing into the inlet of the flow reactor(s) and fluid flowing out of the flow reactor(s) in the conjugation process.

In some embodiments, the temperature control unit includes a heating module arranged at the inlet of the flow reactor(s) and used for heating fluid flowing into the inlet; and a cooling module arranged at the outlet of the flow reactor(s) and used for cooling fluid flowing out of the outlet.

In some embodiments, the conjugation device further includes a sampling detection unit in fluid communication with the outlet of the flow reactor(s) and configured to collect sample fluid from the fluid flowing out of the outlet of the flow reactor(s) according to preset sampling time, and detect a conjugate in the sample fluid to obtain a detection result, wherein the detection result indicates whether the conjugate meets a predefined standard.

In some embodiments, the sampling detection unit includes a sampling pump, a first switching valve, an elution pump, at least one analytical column and a detector. The sampling pump is connected to the outlet of the flow reactor(s) via a sampling tube, a sample loop is arranged on the first switching valve, and the first switching valve is able to switch between a first state and a second state according to the preset sampling time. When the first switching valve is in the first state, the sampling pump is in fluid communication with the sample loop, and to collect the sample fluid from the fluid flowing out of the outlet of the flow reactor(s) via the sampling tube and to pump the sample fluid into the sample loop, and when the first switching valve is in the second state, the elution pump, the sample loop, the at least one analytical column and the detector are in fluid communication via a detection tube, and the elution pump is to pump an eluant into the detection tube to enable the eluant to flow through the sample loop, thereby enabling the sample fluid in the sample loop to flow through one of the at least one analytical column before entering the detector.

In some embodiments, two analytical columns are arranged, and the sampling detection unit further includes a second switching valve able to switch between two states and a washing pump. When the second switching valve is in any of the states, the sample loop and the detector are in fluid communication with one of the two analytical columns, the eluant enables the sample fluid in the sample loop to flow into one analytical column, and the washing pump is in fluid communication with the other analytical column and to pump buffer solution into the other analytical column for equilibrating.

In some embodiments, the first switching valve is a six-way valve, the second switching valve is a ten-way valve, and the elution pump is a quaternary pump.

In some embodiments, the conjugation device further includes a recycling unit arranged between the inlet and the outlet of the flow reactor(s). When the detection result indicates that the conjugate does not meet the predefined standard, the fluid collection unit is configured to stop collection of the fluid flowing out of the outlet of the flow reactor(s), and the recycling unit is configured to control the fluid flowing out of the outlet of the flow reactor(s) to enter the inlet again so as to conduct a re-conjugation reaction in the flow reactor(s).

In some embodiments, the recycling unit includes a seventh valve arranged on a recycling tube. The recycling tube is connected between the inlet and the outlet of the flow reactor, and a recycling container is arranged on the recycling tube. When the detection result indicates that the conjugate does not reach the predefined standard, the seventh valve is opened, and the fluid flowing out of the outlet of the flow reactor flows through the recycling tube and the recycling container and then flows into the inlet.

In some embodiments, the flow reactor is a conjugation column.

In some embodiments, the first moiety includes one of a recognition motif of the ligase acceptor substrate and a recognition motif of the ligase donor substrate, and the second moiety includes the other of the recognition motif of the ligase acceptor substrate and the recognition motif of the ligase donor substrate.

In some embodiments, the conjugation device further includes at least one of: a pressure sensing module, a flow measuring module, a pH metering module, a conductivity metering module and a UV detecting module respectively arranged at the inlet and/or the outlet.

A second aspect of the disclosure provides a method for producing a conjugate, including: providing at least one kind of reaction fluid containing a first moiety and a second moiety of a conjugate to be produced; and producing the conjugate by using any of the conjugation devices in the above embodiments.

In the method for producing the conjugate provided by the second aspect of the disclosure, the ligase is directionally immobilized onto the support and filled into the flow reactor, so that the two moieties of the conjugate to be produced contained in the reaction fluid are continuously and stable conjugated while the reaction fluid passes the fluid reactor. Compared with the chemical conjugation, the conjugation method greatly decreases the process steps, significantly reduces the complexity and is highly suitable to save expensive manufacturing costs. Moreover, by virtue of the flow reactor, linear scale-up of the conjugation process can be realized to satisfy industrial demands for larger scales, unit time for conjugation is shortened, and the occupied space in the manufacturing area is reduced. By using the conjunction method to produce the conjugation, site-specific conjugation between payload-linker and targeting molecule is realized, the homogeneity is improved, and accordingly the therapeutic window is widened. In addition, the conjugation process can be integrated with production procedures of biomolecules such as monoclonal antibodies. For example, conjugation may be completed at stages of producing monoclonal antibody intermediates and monoclonal antibody stock solutions. Therefore, the process is high in flexibility and excellent in coherence.

BRIEF DESCRIPTION OF THE DRAWINGS

The features, advantages and other aspects of various embodiments in the disclosure become more apparent by referring to drawings and in combination with detailed descriptions below. Several embodiments of the disclosure are illustrated in an illustrative manner, rather than a restrictive manner. In the drawings.

DETAILED DESCRIPTION

Technical contents of the present invention are described below by virtue of specific embodiments. Other advantages and effects of the present invention may be easily understood by those skilled in the art by the contents disclosed by the description. The present invention may also be implemented or applied by virtue of other different specific embodiments. Various modifications and changes can be made by those skilled in the art without departing from the spirit of the present invention.

Before describing specific embodiments of the disclosure in detail, some terms used in the disclosure are firstly explained.

General Terms and Definitions

Unless otherwise defined in the following context, meanings of all technical terms and scientific terms used herein are intended to be the same as those generally understood by those skilled in the art. Mentioned techniques involved herein are intended to refer to the commonly understood techniques in the art, including technical changes or replacements of equivalent technologies obvious to those skilled in the art. Although it is believed that the terms herein are well understood by those skilled in the art, the definitions are still stated below so as to well explain the present invention. Trade names that appear herein are intended to refer to corresponding commodities. All patents, disclosed patent applications and publications cited herein are included herein by virtue of reference.

Unless otherwise stated in the context, a singular form such as "one" and "the" includes a plural form. The expression "one or more" or "at least one" may represent 1, 2, 3, 4, 5, 6, 7, 8 and 9 or more.

The term "simultaneously" used herein means one or more events described herein occur at the same time.

The terms such as "include", "contain" and "comprise" and similar terms used herein are open terms, i.e., "include/comprise but not limited to", which represents that other contents may also be included. The term "based on" means "at least partially based on". The term "one embodiment" represents "at least one embodiment". The term "another embodiment" represents "at least another one embodiment".

The term "and/or" used herein (such as in a phrase of A and/or B) is intended to include "A and B", "A or B". "A" and "B". Similarly, the term "and/or" used herein (such as in a phrase of "A, B and/or C") is intended to cover each of implementations as follows: A, B and C; A, B or C; A or C; A or B; B or C; A and C; A and B; B and C; A (alone); B (alone) and C (alone).

The term "connect", "connection", "couple" or "coupled" and other similar words used herein are not limited to direct connection, and may include indirect connection.

Definitions of "biomolecules" used herein cover proteins, nucleic acids, lipids, carbohydrates, small nucleotides, amino acids and derivatives thereof.

The term "ligase" used herein refers to an enzyme that can catalyze covalent bonds of two or more molecules. The ligase may specifically catalyze conjugation between a first moiety including the recognition motif of the ligase donor substrate and a second moiety including the recognition motif of the ligase acceptor substrate, so as to produce a target conjugate.

The term "conjugation" used herein refers to covalent linkage of at least two parties (e.g., at least two molecules or at least two ends of the same molecule).

The term "conjugate" used herein may be prepared by at least two parties (e.g., at least two molecules or at least two ends of the same molecule) by virtue of covalent linkage.

The term "bioconjugate" used herein refers to a conjugate of which at least one conjugation party is a biomolecule. Examples of the bioconjugates include, but not limited to, antibody-drug conjugates, antibody-immune agonist conjugates, antibody-cytokine conjugates, antibody-nuclide conjugates, and the like.

The term "linker" used herein refers to any chemical part that can conjugate a payload to a targeting molecule in a stable covalent manner.

The term "payload" used herein refers to a functional part included in a conjugate linked by the linker. Examples of the payload include, but not limited to small molecule compounds (also called small molecule drugs, such as inhibitors and toxic drugs (e.g., cytotoxic drugs), radionuclide, glycan, nucleic acids and analogues, tracer molecules, and the like. The payload and the linker are covalently linked by an active group so as to obtain a linker-load intermediate.

The term "targeting molecule" used herein refers to a molecule having an affinity for a particular target (such as receptor, cell surface protein, cytokine, etc.). A targeting molecule can deliver the payload to a specific site in-vivo in a targeted manner. A targeting molecule may recognize one or more targets, and its specific target sites are defined by the recognized target. For example, a targeting molecule that targets the receptor can deliver the cytotoxic drug to a site containing lots of the receptors. Examples of the targeting molecules include, but not limited to antibodies, antibody fragments, binding proteins for a given antigen, antibody mimics, scaffolding proteins having affinity to a given target, ligands, and the like.

The term "antibody-drug conjugate (ADC)" used herein refers to a conjugate including an antibody or an antibody fragment that is covalently conjugated to the payload.

The term "small molecule compound" used herein refers to a molecule with a size comparable to that of an organic molecule commonly used in medicine. The term does not encompass biological macromolecules (e.g., proteins, nucleic acids, etc.), but encompasses low molecular weight peptides or derivatives thereof, such as dipeptides, tripeptides, tetrapeptides, pentapeptides, and the like. Typically, the molecular weight of the small molecule compound can be, for example, about 100 Da to about 2000 Da, about 200 Da to about 1000 Da, about 200 Da to about 900 Da, about 200 Da to about 800 Da, about 200 Da to about 700 Da, about 200 Da to about 600 Da, about 200 Da to about 500 Da.

The term "cytotoxin" used herein refers to a substance that inhibits or prevents the expression activity of a cell, cellular function, and/or causes destruction of cells. In some cases, the cytotoxins currently used in ADCs may be more toxic than commonly used chemotherapeutic drugs. Examples of cytotoxins include, but are not limited to, drugs that target the following targets: microtubule cytoskeleton, DNA, RNA, kinesin-mediated protein transport, and regulation of apoptosis.

The term "continuously conjugated" or "continuous conjugation process" used herein means that one or more kinds of reaction fluids needed in the conjugation process are continuously added into the conjugation device when a conjugation reaction is being conducting and at least one conjugate has been produced. The produced conjugate can be continuously collected from the conjugation reaction when the conjugation reaction is being conducting.

The term "flow reactor" used herein refers to any reaction container used for continuously conducting chemical reactions (such as conjugation). The flow reactor may be made of stainless steel, glass, polymer and other materials, and is generally tubular. Flowing reaction fluids enter the flow reactor, continuously conducting a chemical reaction in the flow reactor, and then flow out of the flow reactor.

The term "support" used herein refers to a water-insoluble substance that can be isolated from a reaction mixture in solid or semi-solid form, such as a surface, a gel, a polymer, a matrix, a particle, a resin, a bead or a membrane.

The term "conjugation column" used herein is a kind of flow reactor and refers to a tube-shaped or column-shaped reaction container which is used for continuously conducting conjugation reaction.

The term "online monitoring" or "real-time monitoring" used herein refers to detecting certain parameters or properties, such as pH, pressure, flow, conductivity and conjugation conditions of the moieties, of buffer solution, reaction fluids and fluid flowing out of the flow reactor in real time during use of the conjugation device. Different from offline detection or analysis, the online monitoring or real-time monitoring can provide real-time feedback of the detection result.

Figure 1:
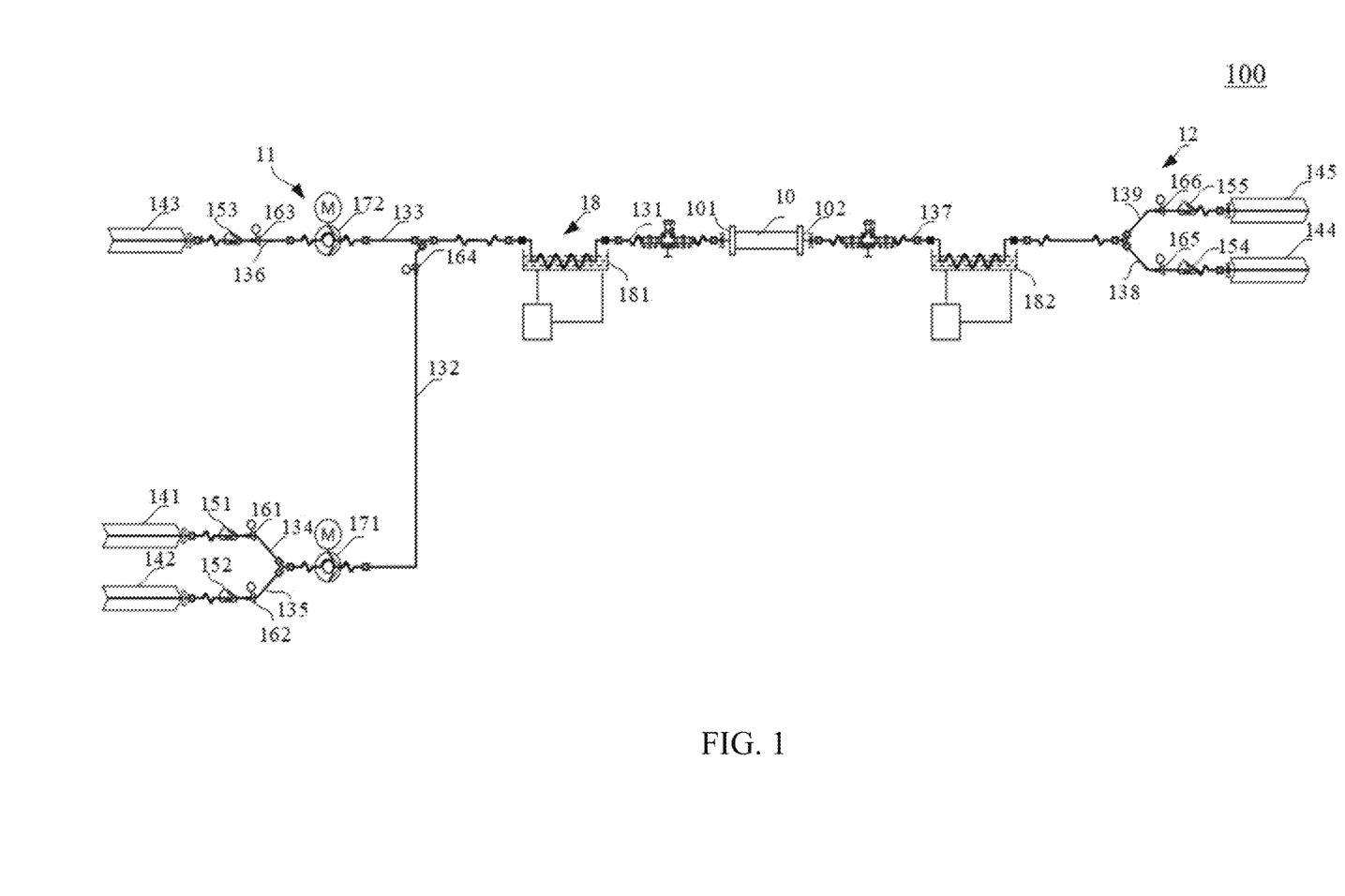
FIG. 1 shows a flow path diagram of a conjugation device according to one embodiment of the disclosure.
Figure 2:
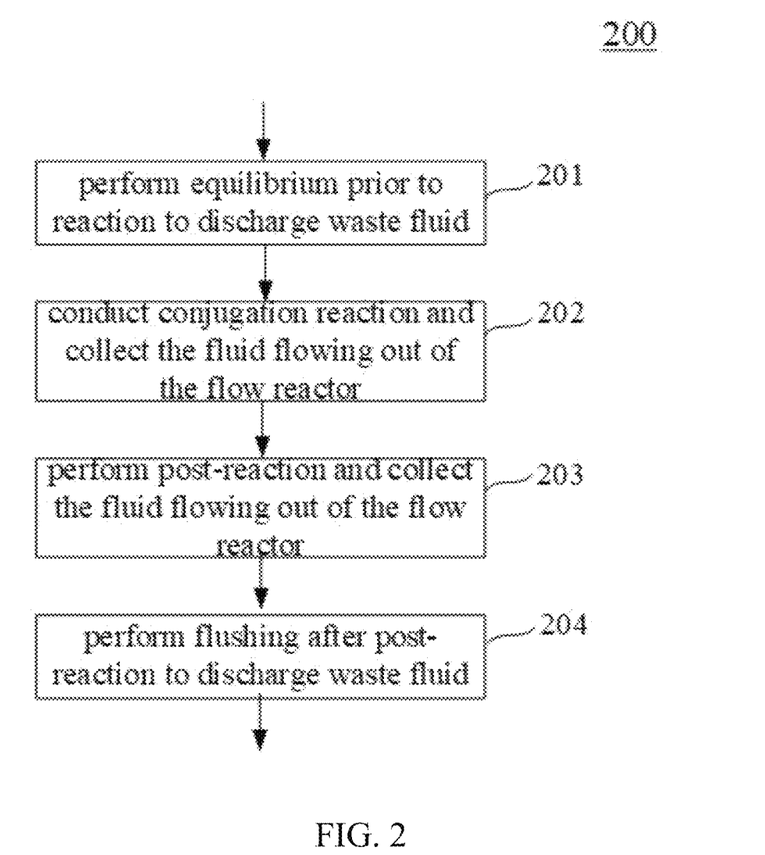
FIG. 2 shows a conjugation process of a conjugation device in FIG. 1.

In the following, one embodiment of the disclosure is described by referring to FIGS. 1 and 2. FIG. 1 shows a flow path diagram of a conjugation device according to one embodiment of the disclosure. FIG. 2 shows a conjugation process of the conjugation device in FIG. 1. For the purpose of illustration, in FIG. 1, various components of the conjugation device 100 are connected via tubes, and connected with five containers used for storing fluids. The ligase is directionally immobilized onto the support such as matrixes and filled in the flow reactor 10. The support and the ligase may be selected according to actual needs. For example, the support may include, but not limited to, fillers such as silica gel, agarose, polyacryl, synthetic fibers, cellulose acetate membranes and polyethersulfone membranes. The ligase may be transpeptidase or glycosidase. The flow reactor 10 has an inlet 101 and an outlet 102. Fluid continuously flows into the inlet 101 of the flow reactor 10, flows through the flow reactor 10, and then continuously flows out of the outlet 102. In this embodiment, the flow reactor 10 is a conjugation column, while in other embodiments, the flow reactor 10 may be any other similar reaction container.

A fluid delivery unit 11 is in fluid communication with the inlet 101 on the inlet 101 side of the flow reactor 10. The fluid delivery unit 11 continuously provides the flow reactor 10 with a first reaction fluid and a second reaction fluid or a buffer solution according to different stages of the conjugation process. A fluid collection unit 12 is in fluid communication with the outlet 102 on the outlet 102 side of the flow reactor 10. The fluid collection unit 12 controls collection of fluid flowing out of the outlet 102 of the flow reactor 10 according to the different stages of the conjugation process. In a period of enabling the first reaction fluid and the second reaction fluid to continuously flow through the flow reactor 10, a conjugation reaction is conducted between a first moiety contained in the first reaction fluid and a second moiety contained in the second reaction fluid under catalysis of the ligase so as to produce a conjugate; and the conjugate is contained in the fluid flowing out of the outlet 102 of the flow reactor 10.

Specifically, as shown in FIG. 1, the inlet 101 of the flow reactor 10 is connected to an inlet main tube 131. Two branch tubes, i.e., a first inlet branch tube 132 and a second inlet branch tube 133, are arranged in parallel, and connected to the inlet main tube 131 via a fluid connector (such as T junction). Openings of a first container 141, a second container 142 and a third container 143 are respectively connected to a first container outlet tube 134, a second container outlet tube 135 and a third container outlet tube 136. The fluid delivery unit 11 includes a first valve 161, a second valve 162, a third valve 163, a fourth valve 164, a first delivery pump 171 and a second delivery pump 172. The first container outlet tube 134 and the second container outlet tube 135 are arranged in parallel, connected together via a fluid connector and connected to the first delivery pump 171. The third container outlet tube 136 is connected to the second delivery pump 172. The first delivery pump 171 and the second delivery pump 172 are respectively connected with the inlet main tube 131 via the first inlet branch tube 132 and the second inlet branch tube 133.

A first pinch valve 151 and the first valve 161 are arranged on the first container outlet tube 134. Similarly, a second pinch valve 152, the second valve 162, a third pinch valve 153 and the third valve 163 are respectively arranged on the second container outlet tube 135 and the third container outlet tube 136. The first pinch valve 151, the second pinch valve 152 and the third pinch valve 153 are all manual pinch valves and are used for controlling outflow of the fluid from the first container 141, the second container 142 and the third container 143. During conjugation preparation, the buffer solution, the first reaction fluid and the second reaction fluid are respectively pumped into corresponding containers by a peristaltic pump. The pinch valves 151-153 are opened during conjugation. Thus, the buffer solution, the first reaction fluid and the second reaction fluid flow out of the corresponding containers. The first valve 161, the second valve 162 and the third valve 163 are respectively used for controlling flow path of the fluid in the first container outlet tube 134, the second container outlet tube 135 and the third container outlet tube 136. A fourth valve 164 is arranged on the first inlet branch tube 132 and is used for controlling flow path of the fluid in the first inlet branch tube 132.

As exciting forces of the fluid, the first delivery pump 171 and the second delivery pump 172 may be pumps of any type, include but not limited to an injection pump, a plunger pump, a peristaltic pump and a diaphragm pump, and may provide different flow rate ranges. For example, some injection pumps may be precision syringe pumps of 1 ml, 10 ml and 50 ml and may provide a flow rate range of 0.01-50 ml/min; some peristaltic pumps may provide a flow rate range of 5-200 ml/min; and some diaphragm pumps may provide a flow rate range of 40-400 ml/min.

Although the first to fourth valves 161-164 for controlling flow path of the buffer solution or the reaction fluids in corresponding tubes are shown in the present embodiment, the fluid delivery unit 11 may only include the first delivery pump 171 and the second delivery pump 172 in other embodiments, and the first to fourth valves 161-164 are not needed. For example, when the first delivery pump 171 and the second delivery pump 172 are plunger pumps or diaphragm pumps, the first to fourth valves 161-164 are not needed.

By continuously referring to FIG. 1, the outlet 102 of the flow reactor 10 is connected to an outlet main tube 137. Openings of a fourth container 144 and a fifth container 145 are respectively connected to a fourth container inlet tube 138 and a fifth container inlet tube 139. The fluid collection unit 12 includes a fifth valve 165 and a sixth valve 166. The fifth valve 165 and the sixth valve 166 are respectively arranged on the fourth container inlet tube 138 and the fifth container inlet tube 139. In addition, a fourth pinch valve 154 is arranged on the fourth container inlet tube 138. Similarly, a fifth pinch valve 155 is arranged on the fifth container inlet tube 139. Identical to the first to third pinch valves 151-153 described above, both of the fourth pinch valve 154 and the fifth pinch valve 155 are manual pinch valves and are used for controlling outflow of the fluid from the fourth container 144 and the fifth container 145. A fifth valve 165 and a sixth valve 166 are respectively used for controlling flow path of the fluid in the fourth container inlet tube 138 and the fifth container inlet tube 139. The fourth container inlet tube 138 and the fifth container inlet tube 139 are connected with the outlet main tube 137 via a fluid connector.

The first to sixth valves 161-166 may be valves of any type, such as a pneumatic valve, an electrical valve and a hydraulic valve, etc. Preferably, the first to sixth valves 161-166 are electromagnetic valves.

The form, material and capacity of the first to fifth containers 141-145 may be selected according to actual needs, such as disposable liquid storage bags, disposable liquid storage bottles, stainless steel containers, and both disposable and non-disposable glass or plastic containers of different specifications. Meanwhile, materials and specifications (such as inner diameters) of the tubes connected among the various components of the conjugation device 100 may be selected according to actual needs. The tubes may be made of silicone, titanium, stainless steel, or any other suitable materials. For example, the first to third container outlet tubes 134-136, the fourth and fifth container inlet tubes 138 and 139 and the outlet tube 137 are disposable silicone tubes of normal thicknesses, while the inlet main tube 131 and the first and second inlet branch tubes 132 and 133 are disposable silicone tubes of increased thicknesses. Thus, higher flow and pressures can be borne. Preferably, the first to fifth containers 141-145 and the various tubes are a set of the disposable silicone tubes and disposable liquid storage bags and can directly be used as sterilized (such as by gamma ray irradiation) tubes and bags. The set of the disposable silicone tubes and liquid storage bags can be in a plug-and-play manner on the conjugation device 100, which avoids repeated cleaning and are convenient to use. Therefore, a fully closed system required by drug production can be conveniently matched; and the drugs can be prevented from being suffered from external pollution in the production process. In other embodiments, the first to fifth containers 141-145 and the tubes connected among various components of the conjugation device 100 are made of stainless steel, which may be used repeatedly by applying cleaning validation. In these embodiments, the production cost can be reduced and the working life of the containers and the tubes can be extended.

In addition, the conjugation device 100 shown in FIG. 1 further includes a temperature control unit 18. In the present embodiment, the temperature control unit 18 includes a heating module 181 arranged on the inlet main tube 131 and a cooling module 182 arranged on the outlet main tube 137. The heating module 181 and the cooling module 182 are used for respectively heating and cooling the inlet main tube 131 and the outlet main tube 137. The heating module 181 heats the fluid flowing into the inlet 101 of the flow reactor 10 to an appropriate reaction temperature (e.g. 37° C.) and the cooling module 182 cools the fluid flowing out of the flow reactor 10 to an appropriate temperature (e.g. room temperature). The temperature control ranges, flow rates and materials of the heating module 181 and the cooling module 182 may be selected according to actual needs. For example, the temperature control range of the heating module 181 is 20-60° C., the temperature control range of the cooling module 182 is 10-30° C., and the heating module 181 and the cooling module 182 are both of stainless steel sanitary grades or disposable materials. In the other embodiments, the temperature control unit 18 may be of other forms, including but not limited to air heating temperature control, water bath temperature control (i.e. the flow reactor 10 is placed in a water bath), jacket water bath temperature control (i.e. the outer part of the flow reactor 10 sleeves with a jacket, and water at a fixed temperature circulates in the jacket), and coil winding temperature control, etc.

In the conjugation device 100 in FIG. 1, the buffer solution is stored in the first container 141, and the first reaction fluid and the second reaction fluid are respectively stored in the second container 142 and the third container 143. However, in other embodiments, the reaction fluids and the buffer solution may be stored in the containers in a different way according to actual needs. The number of the containers storing the reaction fluids or the buffer solution may also be expanded according to actual needs. For example, more containers and container outlet tubes as well as pinch valves and valves are increased in parallel with the first container 141, the second container 142 and/or the third container 143. Correspondingly, the reaction fluid or the buffer solution needing to be pumped is selected by the first delivery pump 171 and the second delivery pump 172 according to process procedures. In other embodiments, the numbers of the transfer pumps may be selected according to actual needs, e.g., a corresponding transfer pump is equipped for each container.

The first reaction fluid includes the first moiety of the conjugate to be produced, and the second reaction fluid includes the second moiety of the conjugate. The reaction fluid may be liquid or gas. The first moiety includes one of a recognition motif of the ligase acceptor substrate and a recognition motif of the ligase donor substrate, and the second moiety includes the other of the recognition motif of the ligase acceptor substrate and the recognition motif of the ligase donor substrate. In the present embodiment, the first moiety further includes targeting molecules, such as antibodies, antibody fragments, antigen-specified binding proteins and artificial antibodies. The second moiety further includes a linker-payload intermediate formed by coupling molecules of cytokines, small molecule toxins and nuclides with a linker, and the produced conjugate is a bioconjugate. In other embodiments, the first moiety and the second moiety may include molecules of other types, as long as one molecule has the recognition motif of the ligase acceptor substrate and the other molecule has the recognition motif of the ligase donor substrate.

In one embodiment, the ligase is a transpeptidase. In one embodiment, the ligase is selected from the group consisting of a natural transpeptidase, an unnatural transpeptidase, variants thereof, and the combination thereof. Unnatural transpeptidase enzymes can be, but are not limited to, those obtained by engineering of natural transpeptidase. In a preferred embodiment, the ligase is selected from the group consisting of a natural Sortase, an unnatural Sortase, and the combination thereof. The species of natural Sortase include Sortase A, Sortase B, Sortase C, Sortase D, Sortase *L. plantarum*, etc. (see U.S. 20110321183A1). The type of ligase corresponds to the ligase recognition motif and is thereby used to achieve specific coupling between different molecules or structural fragments. In one embodiment, the recognition motif of the ligase acceptor substrate is selected from the group consisting of oligomeric glycine, oligomeric alanine, and a mixture of oligomeric glycine/alanine having a degree of polymerization of 3-10. In a particular embodiment, the recognition motif of the ligase acceptor substrate is Gn, wherein G is glycine (Gly), and n is an integer of 3 to 10. In another particular embodiment, the ligase is Sortase A from *Staphylococcus aureus*. Accordingly, the ligase recognition motif can be the typical recognition motif LPXTG of the enzyme. In yet another particular embodiment, the recognition motif of the ligase donor substrate is LPXTGJ, and the recognition motif of the ligase acceptor substrate is $G_n$, wherein X can be any single amino acid that is natural or unnatural; J is absent, or is an amino acid fragment comprising 1-10 amino acids, optionally labeled. In one embodiment, J is absent. In yet another embodiment, J is an amino acid fragment comprising 1-10 amino acids, wherein each amino acid is independently any natural or unnatural amino acid. In another embodiment, J is $G_m$, wherein m is an integer of 1 to 10. In yet another particular embodiment, the recognition motif of the ligase donor substrate is LPETG. In another particular embodiment, the recognition motif of the ligase donor substrate is LPETGG. In one embodiment, the ligase is Sortase B from *Staphylococcus aureus* and the corresponding recognition motif of the donor substrate can be NPQTN. In another embodiment, the ligase is Sortase B from *Bacillus anthracis* and the corresponding recognition motif of the donor substrate can be NPKTG. In yet another embodiment, the ligase is Sortase A from *Streptococcus pyogenes* and the corresponding recognition motif of the donor substrate can be LPXTGJ, wherein J is as defined above. In another embodiment, the ligase is Sortase subfamily 5 from *Streptomyces coelicolor*, and the corresponding recognition motif of the donor substrate can be LAXTG. In yet another embodiment, the ligase is Sortase A from *Lactobacillus plantarum* and the corresponding recognition motif of the donor substrate can be LPQTSEQ. The ligase recognition motif can also be other artificially designed recognition sequence for transpeptidase optimized by manual screening.

In other embodiments, the first reaction fluid and the second reaction fluid may be mixed before being conjugated by using the conjugation device 100. In such embodiments, the mixture of the first reaction fluid and the second reaction fluid is pumped into the second container 142 or the third container 143 in the conjugation preparation process. In the conjugation process, only the container storing the mixture and its associated tubes and components are used. Alternatively, the conjugation device 100 may only include one of the second container 142 and the third container 143 and its associated tubes and components.

Then, the conjugation process 200 of the conjugation device 100 is described by referring to FIGS. 1 and 2. In the conjugation process 200 of FIG. 2, step 201 includes performing equilibrium prior to reaction on the flow reactor 10 to discharge waste fluid. At this stage, the first valve 161, the fourth valve 164 and the fifth valve 165 are all in an opened state, while the other valves are all closed. The buffer solution in the first container 141 continuously flows out of the first container 141 under the control of the first delivery pump 171 and enters the inlet main tube 131 after flowing through the first container outlet tube 134 and the first inlet branch tube 132. The outflow speed and duration of the buffer solution may be determined by presetting a pump speed and operating time of the first delivery pump 171. During the process of flowing into the inlet main tube 131, the buffer solution flows into the heating module 181 and is preheated by the heating module 181. After flowing out of the heating module 181, the buffer solution flows into the inlet 101 of the flow reactor 10, so as to equilibrate the flow reactor 10. Later, the buffer solution flows out of the outlet 102 of the flow reactor 10, through the outlet main tube 137 and into the cooling module 182 for post-cooling, and then is discharged into the fourth container 144 via the fourth container inlet tube 138 so as to collect the waste fluid. By equilibrating the flow reactor 10 before providing the first reaction fluid and the second reaction fluid, a reaction environment of an appropriate pH and ion strength can be provided for the flow reactor 10.

Then, at step 202, a conjugation reaction is conducted and the fluid flowing out of the flow reactor 10 is collected. At this stage, the first valve 161 and the fifth valve 165 are switched to a closed state and the fourth valve 164 is maintained in an opened state, while the second valve 162, the third valve 163 and the sixth valve 166 are switched to an opened state. The first reaction fluid in the second container 142 continuously flows out of the second container 142 under the control of the first delivery pump 171 and flows through the second container outlet tube 135 and the first inlet branch tube 132. The second reaction fluid in the third container 143 continuously flows out of the third container 143 under the control of the second delivery pump 172 and flows through the third container outlet tube 136 and the second inlet branch tube 133. The flow rates of the first reaction fluid and the second reaction fluid are determined by respectively presetting the pump speeds of the first delivery pump 171 and the second delivery pump 172. According to different process requirements, the conjugation flow rate and the flow rate of each kind of reaction fluid (such as ½ conjugation flow rate) are calculated by dividing a reaction volume of the flow reactor 10 by retention time of the reaction fluid in the flow reactor 10.

The two kinds of reaction fluid are then merged in the inlet main tube 131, preheated in the heating module 181 and then flow into the inlet 101 of the flow reactor 10. In the flow reactor 10, a conjugation reaction is conducted between the first moiety contained in the first reaction fluid and the second moiety contained in the second reaction fluid by virtue of catalysis of the ligase, and the conjugate is produced. Meanwhile, the reacted fluid containing the conjugate continuously flows out of the outlet 102 of the flow reactor 10. The fluid flowing out of the outlet 102 of the flow reactor 10 is post-cooled in the cooling module 182 and then flows into the fifth container 145 via the fifth container inlet tube 139 so as to collect the conjugate. It should be noted that, since the first reaction fluid and the second reaction fluid are continuously provided to the flow reactor 10, the above conjugation reaction is a continuous conjugation reaction. Theoretical conjugation time may be calculated by dividing the relatively small volume of the first reaction fluid and the second reaction fluid by the flow rate of the reaction fluid. The operating time of the first delivery pump 171 and the second delivery pump 172 is set to be longer than the theoretical conjugation time in advance.

After the conjugation reaction, there still exists a small part of unreacted and being-reacted reaction fluid in each tube and the flow reactor 10, and therefore the tubes and the flow reactor 10 shall be flushed, so that the unreacted and being-reacted reaction fluid can be reacted as much as possible and then collected. Therefore, step 203 includes performing post-reaction, and the fluid flowing out of the flow reactor 10 is collected. At this stage, the first valve 161 is switched to the opened state, the second valve 162 and the third valve 163 are switched to the closed state, the fourth valve 164 and the sixth valve 166 are maintained in the opened state, and the fifth valve 165 is maintained in the closed state. The buffer solution in the first container 141 continuously flows out of the first container 141 under the control of the first delivery pump 171, through the first container outlet tube 134 and the first inlet branch tube 132 and then enters the inlet main tube 131. Similarly, the outflow rate and duration of the buffer solution may be determined by presetting the pump speed and the operating time of the first delivery pump 171. Later, the buffer solution flows into the heating module 181 and is preheated by the heating module 181. After flowing out of the heating module 181, the buffer solution flows into the inlet 101 of the flow reactor 10, so as to flush the flow reactor 10. Then, the buffer solution flows out of the outlet 102 of the flow reactor 10, flows into the cooling module 182 via the outlet main tube 137 for post-cooling, and then flows into the fifth container 145 via the fifth container inlet tube 139 so as to continue to collect the conjugate. By performing post-reaction with the buffer solution after the conjugation reaction is ended, the residual reaction fluid in the tubes and the flow reactor can be fully utilized, thereby increasing yield.

After step 203, flushing after post-reaction is performed in step 204, and the waste fluid is discharged. At this stage, both of the first valve 161 and the fourth valve 164 are maintained in the opened state, the fifth valve 165 is switched to the opened state, the sixth valve 166 is switched to the closed state, and the states of the second valve 162 and the third valve 163 are maintained in the closed state. The buffer solution in the first container 141 continue to flow out of the first container 141 under the control of the first delivery pump 171, flows through the first container outlet tube 134 and the first inlet branch tube 132 and then enters the inlet main tube 131. Similarly, the outflow rate and the duration of the buffer solution may be determined by presetting the pump speed and the operating time of the first delivery pump 171. Later, the buffer solution is preheated in the heating module 181, enters the inlet 101 of the flow reactor 10 and continues to flush the flow reactor 10. Then, the buffer solution flows out of the outlet 102 of the flow reactor 10, flows into the cooling module 182 via the outlet main tube 137 for post-cooling, and is discharged into the fourth container 144 via the fourth container inlet tube 138 so as to collect the waste fluid. By providing the buffer solution after the stage of flushing after post-reaction, residues in the tubes and the flow reactor can be fully flushed.

The above first to sixth valves 161-166, the first delivery pump 171 and the second delivery pump 172 can be controlled by a control signal, thereby enabling them to cooperate with each other. In the present embodiment, control units or processing units of the above components are commutatively coupled to a computing device. The computing device and the conjugation device form a physically integral conjugation system. In other embodiments, the computing device may be positioned away from the conjugation device, such as a remote computing device. The computing device is commutatively coupled to the above components via analog, digital or combined analog/digital buses or via a wireless communication link or network, and may be a computing device of any type, such as a server, a workstation or a portable computing device (e.g., a laptop, a tablet personal computer and a mobile phone). The computing device and the various components respectively store multiple applications to be executed by them. The computing device receives signals or other information related to the components from respective components, and executes a control application. The control application makes a control decision and generates one or more control signals based on the received information. Then, the control application transmits the one or more control signals to the various components via the communication link or network, thereby controlling operations of the components. By using a configuration application in the computing device, the operator is able to create or modify setup parameters in the control application via a user interface before the conjugation process starts, such as starting and ending time of each stage in the conjugation process and flow rates of the fluid. The setup parameters may be determined by the operator based on instances of the reaction fluids in specific process design and conditions needed by conjugation. A view application in the computing device receives data from the control application, and displays the data to the operator via the user interface. For example, the data may include the current flow rate, the state of each valve, the pump speed of each delivery pump, the temperature of the inlet fluid, the temperature of the outlet fluid, and the like. Thus, in the conjugation process 200, a real-time state of the conjugation device can be monitored by the production personnel. A data historian application in the computing device receives data from the configuration application and the control application, and stores historical data including personnel historical operations in the conjugation process 200 and historical parameters and conjugation results in the conjugation process 200 in a storage of the computing device. The steps 201-204 in the conjugation process 200 can be performed automatically and continuously without human intervention.

In the above embodiments, the ligase is directionally immobilized onto the support and filled into the flow reactor, so that the two moieties of the conjugate to be produced contained in the reaction fluid are continuously and stably conjugated while the reaction fluid passes the fluid reactor. Compared with the chemical conjugation, the conjugation device greatly decreases the process steps, significantly reduces the complexity and is highly suitable to save expensive manufacturing costs. Moreover, by virtue of the flow reactor, linear scale-up of the conjugation process can be realized to satisfy industrial demands for larger scales, unit time for conjugation is shortened; and the occupied space in the manufacturing area is reduced. By producing the bioconjugates using the conjugation device, site-specific conjugation between payload-linker and targeting molecule is realized, the homogeneity is improved, and accordingly the therapeutic window is widened. In addition, the conjugation process can be integrated with production procedures of biomolecules such as monoclonal antibodies. For example, conjugation may be completed at stages of producing monoclonal antibody intermediates and monoclonal antibody stock solutions. Therefore, the process is high in flexibility and excellent in coherence.

Figure 3:
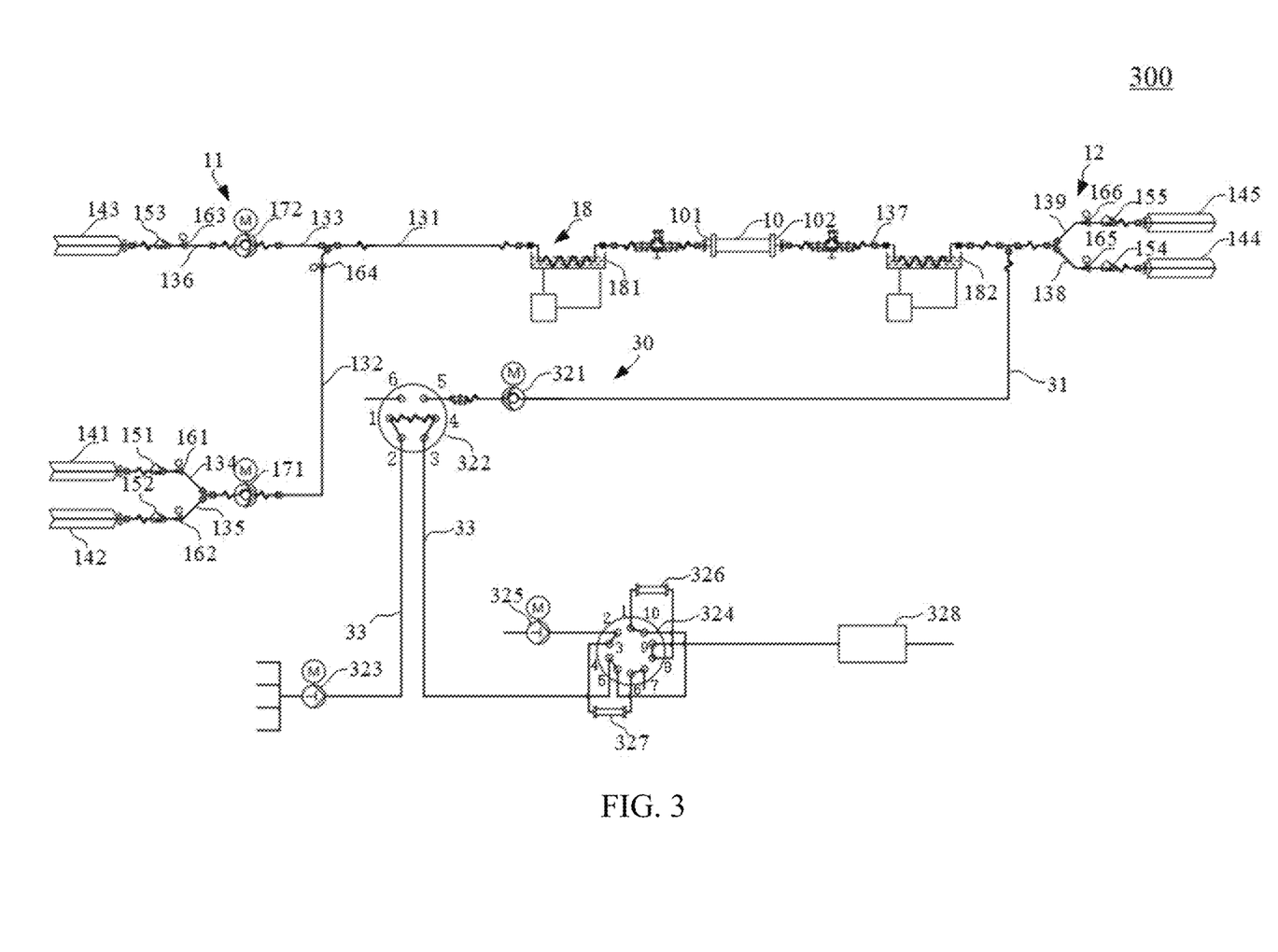
FIG. 3 shows a flow path diagram of a conjugation device according to another embodiment of the disclosure.
Figure 4:
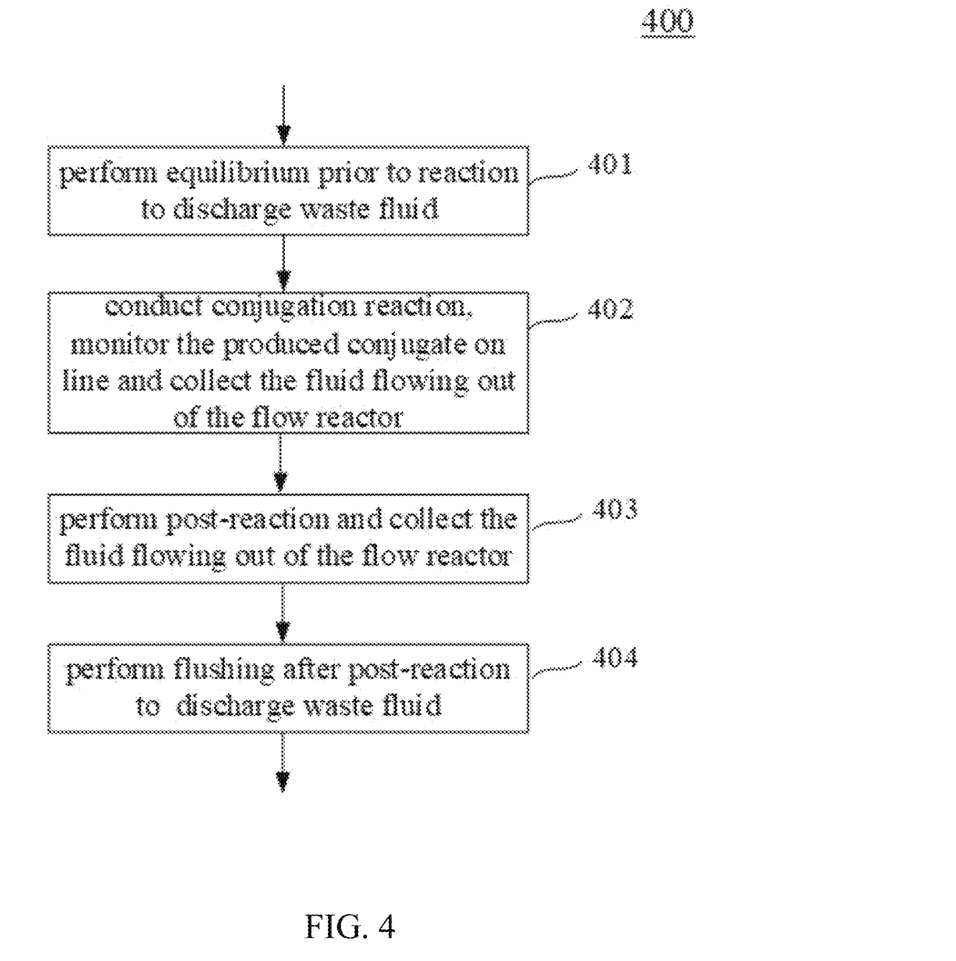
FIG. 4 shows a conjugation process of a conjugation device in FIG. 3.

In the following, another embodiment of the present disclosure is described with reference to FIGS. 3 and 4. FIG. 3 shows a flow path diagram of a conjugation device in another embodiment of the disclosure. FIG. 4 shows a conjugation process of the conjugation device in FIG. 3. In FIG. 3, reference numerals identical to those in FIG. 1 identify the same features as those described with reference to FIG. 1. Compared with FIG. 1, the flow path diagram of the conjugation device 300 in FIG. 3 further includes a sampling detection flow path, while the conjugation flow path in FIG. 3 is the same as FIG. 1 and will not be described.

The conjugation device 300 in FIG. 3 includes a sampling detection unit 30 in fluid communication with the outlet 102 of the flow reactor 10. The sampling detection unit 30 collects sample fluid from the fluid flowing out of the outlet 102 of the flow reactor 10 according to preset sampling time, and detects the conjugate in the sample fluid to obtain a detection result indicating whether the conjugate meets a predefined standard. Specifically, in the present embodiment, the sampling detection unit 30 includes a sampling pump 321, a first switching valve 322, an elution pump 323, a washing pump 325, a first analytical column 326, a second analytical column 327 and a detector 328. The sampling pump 321 is connected to the outlet tube 137 via a sampling tube 31. The first switching valve 322 is connected to the sampling pump 321. In the present embodiment, the first switching valve 322 is a six-way valve on which a sample loop is arranged. The first switching valve 322 is switched between two states for sample injection and sample delivery. The first switching valve 322 is connected to the elution pump 323 and the second switching valve 324 via a detection tube 33. In the present embodiment, the second switching valve 324 is a ten-way valve. The first analytical column 326 and the second analytical column 327 are connected in parallel to form a dual-column sample injection mode. By switching the second switching valve 324 between two states, one of the first analytical column 326 and the second analytical column 327 is selected so as to allow the sample fluid to flow through. The washing pump 325 pumps the buffer solution when the sample fluid flows through the selected analytical column, so that the buffer solution flows through the other analytical column so as to equilibrate the other analytical column.

As shown in FIG. 3, the first switching valve 322 includes 6 ports 1-6 as well as a sample injection state and a sample delivery state. The second switching valve 324 includes 10 ports 1-10 as well as an equilibrium state and a detection state. Connections of the various ports of the first switching valve 322 are as follows: port 1 and port 4 are connected by externally connecting a sample injection loop; port 2 is connected to the elution pump 323; port 3 is connected to port 4 of the second switching valve 324; port 5 is connected to the sampling pump 321; and port 6 is connected to a waste discharge tube. Connections of the various ports of the second switching valve 324 are as follows: port 1 and port 8 are respectively connected to two ends of the first analytical column 326; port 2 is connected to the washing pump 325; port 3 and port 6 are respectively connected to two ends of the second analytical column 327; port 4 is connected to port 3 of the first switching valve 322; port 5 is connected to port 10; port 7 is connected to the waste discharge tube; and port 9 is connected to an inlet of the detector 328.

Referring to FIG. 4, compared with the conjugation method 200 in FIG. 2, steps 401 and 403-404 in the conjugation method 400 are respectively identical to steps 201 and 203-204 in FIG. 2, the only difference in FIGS. 2 and 4 is step 402. For this reason, only step 402 is described with reference to FIG. 3, while description of steps 401 and 403-404 will be eliminated.

Step 402 includes conducting the conjugation reaction and performing online monitoring of the produced conjugate to determine whether the produced conjugate meets the predefined standard. In the process of the conjugation reaction, the sampling pump 321 collects predetermined quantity of sample fluid from the outlet main tube 137 according to the preset sampling time. At this time, the first switching valve 322 is in the first state (the sample injection state). In this state, port 5 and port 4 of the first switching valve 322 are communicated with each other; port 1 is communicated with port 6; and port 2 is communicated with port 3. Since port 1 is communicated with port 4 via the sample loop, the flow path of the sample fluid is as follows: port 5—port 4—sample loop—port 1—port 6. In this way, the sample fluid is pumped in and stored in the sample loop, and excessive sample fluid is discharged from port 6, thereby completing sampling. Specifications of the sample loop can be selected based on different detection methods and the volume of the sample fluid needed for each sampling, such as 5 µL, 10 µL, 20 µL and 30 µL. Meanwhile, the elution pump 323 pumps the buffer solution to port 2 of the first switching valve 322 via a detection tube 33, the buffer solution flows out of port 3 and then flows into port 4 of the second switching valve 324. At this time, the second switching valve 324 is in the first state, port 4 of the second switching valve 324 is communicated with port 5; port 8 is communicated with port 9; port 10 is communicated with port 1; and port 2 is communicated with port 3. The flow path of the inflow buffer solution in the second switching valve 324 is as follows: port 4—port 5—port 10—port 1—first analytical column 326—port 8—port 9—detector 328, so as to pre-equilibrate the first analytical column 326. The inlet tube of the washing pump 325 receives equilibration buffer solution, and therefore the equilibration buffer solution is pumped into port 2 of the second switching valve 324. The flow path of the equilibration buffer solution in the second switching valve 324 is as follows: port 2—port 3—second analytical column 327—port 6—port 7—waste discharge, so as to equilibrate the second analytical column 327.

The first switching valve 322 is switched to the second state (i.e. the sample delivery state) after sampling. In the second state, port 1 of the first switching valve 322 is communicated with port 2; port 3 is communicated with port 4; and port 5 is communicated with port 6. Therefore, the flow path of the sample fluid is as follows: elution pump 323—port 2—port 1—sample loop—port 4—port 3—port 4 of the second switching valve 324. After entering the second switching valve 324, the flow path of the sample fluid is as follows: port 4—port 5—port 10—port 1—first analytical column 326—port 8—port 9—detector 328. In the present embodiment, the elution pump 323 is a quaternary pump and controls a ratio of four eluants and pumps the eluants into the detection tube 33, so that the eluants flow through the sample loop between port 1 and port 4 of the first switching valve 322, thereby enabling the sample fluid in the sample loop to enter the second switching valve 324. The sample fluid is eluted in the first analytical column 326 by controlling gradients of the eluants by the elution pump 323, and the fluid flowing out of the first analytical column 326 enters the detector 328 for detecting the conjugate.

Valve position of the second switching valve 324 is switched for the next sample injection, i.e., port 1 is communicated with port 2; port 3 is communicated with port 4; port 5 is communicated with port 6; port 7 is communicated with port 8; and port 9 is communicated with port 10. In this valve position, the fluid flowing from port 4 of the second switching valve 324 flows through port 3 and enters the second analytical column 327, and then flows out of the second analytical column 327 and sequentially flows through port 6, port 5, port 10 and port 9 to enter the detector 328. Meanwhile, the first analytical column 326 is equilibrated by the buffer solution pumped by the cleaning pump 325.

The detection result obtained by the detector 328 indicates whether the conjugate meets the predefined standard. In the process of the conjugation reaction, the sampling pump 321 collects the sample fluid according to the preset sampling time (e.g. a fixed time interval) and detects the conjugate contained in the sample fluid in real time, thereby monitoring the conjugate produced in the whole conjugation process on line. When the ADC drug is produced by the conjugation device 300 in FIG. 3, the mean DAR value of the ADC is detected for evaluating an average number of small molecule toxins conjugated to each antibody molecule. Thus, the quality of the conjugate can be rated. The detection result may also be transmitted to control units of the fifth valve 165 and the sixth valve 166, so that opening and closing of the fifth valve 165 and the sixth valve 166 can be controlled according to the detection results. Under this circumstance, after the flow reactor 10 is equilibrated and the conjugation reaction just starts, the fifth valve 165 is maintained in the opened state, while the sixth valve 166 is maintained in the closed state. The sampling pump 321 collects the sample fluid from the fluid in the outlet main tube 137 and the conjugate in the sample fluid is detected. When the conjugate meets the predefined standard, the fifth valve 165 is switched to the closed state, while the sixth valve 166 is switched to the opened state, and the fluid in the outlet main tube 137 is collected into the fifth container 145.

The above described first to sixth valves 161-166, the first delivery pump 171 and the second delivery pump 172 are identical to those in the conjugation device 100 in FIG. 1. The control units or processing units of the various components are commutatively coupled to one computing device. The device further enables control and integration of the sampling pump 321. Control units or processing units of the first switching valve 322, the elution pump 323, the second switching valve 324 and the detector 328 are commutatively coupled to the same computing device, thereby enabling them to cooperate with each other. In addition to the above described content, in the present embodiment, the detector 328 transmits the obtained detection result to the control application in the computing device, and the control application determines whether the conjugate meets the predefined standard based on the detection result. Setup parameters in the control application may further include sampling start time, fixed sampling interval, the pump speed of the sampling pump, the pump speed of the elution pump, the pump speed of the washing pump, valve position switching time of each switching valve, eluant gradient, detecting time, the predefined standard of the conjugate (e.g. a preset DAR value), and the like. The view application in the computing device further displays real-time data of the above parameters received from the control application via the user interface.

In the present embodiment, the detector 328 is a UV detector (ultraviolet absorption detector). Both the first analytical column 326 and the second analytical column 327 are HIC (hydrophobic interaction chromatography) analytical columns. Efficiency of the conjugate is detected by an HIC-HPLC (High Performance Liquid Chromatography) detection method. In other embodiments, the efficiency of the conjugate may be detected by other detection methods such as RP-HPLC, SEC-HPLC and Protein A-HPLC. Alternatively, the detector 328 may be a mass spectrometry detector or a fluorescence detector, etc. In the present embodiment, dual-column detection is used, and flow paths in the two analytical columns are switched by the second switching valve 324. In other embodiments, analytical columns of other numbers may also be used. For example, only one analytical column is arranged, and in this case, the second switching valve 324 is not needed any more.

In the present embodiment, active sampling is conducted from the outlet main tube 137 by the sampling pump 321 via the sampling tube 31. The sampling pump 321 may be a peristaltic pump or an injection pump, so that the sampling volume can be accurately controlled and decreased, and thus the product yield can be increased. In other embodiments, instead of using the sampling pump 321, one valve is arranged on the sampling tube 31. By switching the valve position of the valve, fluid in the outlet main tube 137 flows into the sampling tube 31 and enters the sample loop of the first switching valve 322.

By adding the sampling detection unit in the conjugation device 300, whether the conjugate produced in the flow reactor meets the predefined standard can be monitored on line, thereby facilitating collection of the reacted fluid meeting the standard, decreasing the processing time and cost as well as increasing the product consistency. Moreover, manual sampling by the operator in the conjugation process is no longer needed, and thus process convenience is increased, operating complexity is decreased, and possible human errors are avoided.

In the above embodiments, the ligase is directionally immobilized onto the support and filled into the flow reactor, so that the two moieties of the conjugate to be produced contained in the reaction fluid are continuously and stably conjugated while the reaction fluid passes the fluid reactor. Compared with the chemical conjugation, the conjugation device greatly decreases the process steps, significantly reduces the complexity and is highly suitable to save expensive manufacturing costs. Moreover, by virtue of the flow reactor, linear scale-up of the conjugation process can be realized to satisfy industrial demands for larger scale s, unit time for conjugation, and the occupied space in the manufacturing area is reduced. By producing the bioconjugates using the conjugation device, site-specific conjugation between payload-linker and targeting molecule is realized, the homogeneity is improved, and accordingly the therapeutic window is widened. In addition, the conjugation process can be integrated with production procedures of biomolecules such as monoclonal antibodies. For example, conjugation may be completed at stages of producing monoclonal antibody intermediates and monoclonal antibody stock solutions. Therefore, the process is high in flexibility and excellent in coherence.

Figure 5:
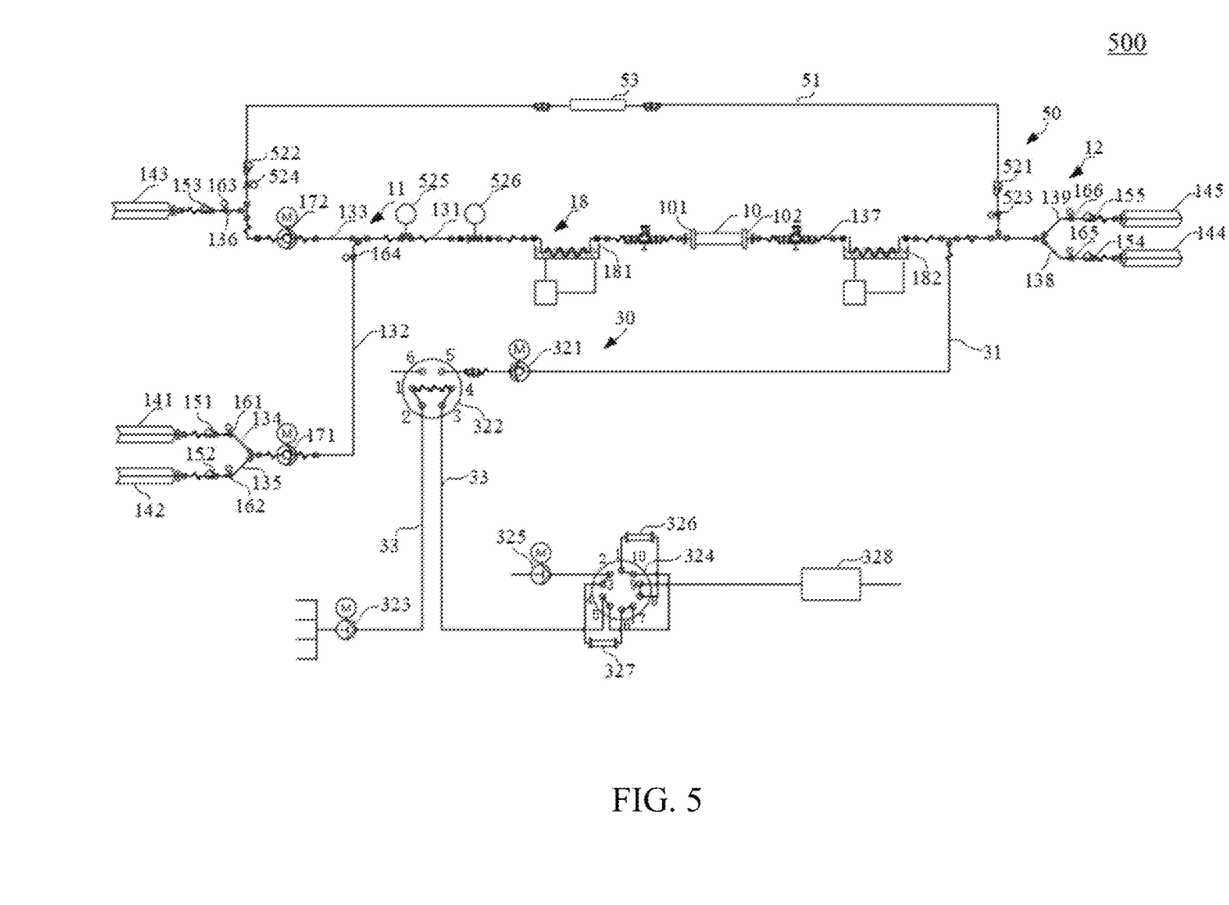
FIG. 5 shows a flow path diagram of a conjugation device according to yet another embodiment of the disclosure.

In the following, a yet another embodiment of the present disclosure is described with reference to FIG. 5. FIG. 5 shows a flow path diagram of a conjugation device in the further embodiment of the disclosure. In FIG. 5, reference numerals identical to those in FIGS. 1 and 3 identify the same features as those described with reference to FIGS. 1 and 3.

Compared with FIG. 3, the flow path diagram of the conjugation device 500 in FIG. 5 further includes a recycling flow path. In the flow path diagram of FIG. 5, a recycling unit 50 is arranged between the inlet 101 and the outlet 102 of the flow reactor 10. In the process of the conjugation reaction, when the detection result obtained by the detector 328 indicates that the conjugate does not meet the predefined standard, the fluid collection unit 12 stops collection of the fluid flowing out of the outlet 102 of the flow reactor 10. Moreover, the recycling unit 50 controls the fluid flowing out of the outlet 102 of the flow reactor 10 to enter the inlet 101 again, so that the fluid conducts a cyclic conjugation reaction in the flow reactor 10.

Specifically, in FIG. 5, in addition to connection with the sampling tube 31, the outlet main tube 137 is also connected to one end of a circulating tube 51. The other end of the circulating tube 51 and the third container outlet tube 136 are both connected to the second inlet tube 133 via a fluid connector. A recycling container 53, a sixth pinch valve 521, a seventh pinch valve 522, a seventh valve 523 and an eighth valve 524 are arranged on the circulating tube 51.

The recycling container 53 is used for storing reaction fluid that does not meet the predefined standard. Similar to the first to fifth containers 141-145, the form, material and capacity of the recycling container 53 may be selected according to actual needs, such as disposable liquid storage bags, disposable liquid storage bottles, stainless steel containers and both disposable and non-disposable glass or plastic containers of different specifications. The material and specification (such as the inner diameter) of the circulating tube 51 may be selected according to actual needs, such as a disposable silicone tube of normal thickness. Preferably, the recycling container 53, the first to fifth containers 131-135 and the various tubes are a set of the disposable silicone tubes and the liquid storage bags.

Both the seventh pinch valve 521 and the eighth pinch valve 522 are manual pinch valves and are used for controlling inflow and outflow of the fluid in the recycling container 53. The seventh valve 523 and the eighth valve 524 are used for controlling flow path of the fluid in the circulating tube 51 in the circulating conjugation process. Similar to the first to sixth valves 161-166, the seventh valve 523 and the eighth valve 524 may be valves of any type, such as a pneumatic valve, an electrical valve and a hydraulic valve. Preferably, the seventh valve 523 and the eighth valve 524 are electromagnetic valves.

In the process of the conjugation reaction, the sampling pump 321 collects predetermined quantity of sample fluid from the outlet main tube 137 according to the preset sampling time. The sample fluid enters the second switching valve 324 by the cooperation of the elution pump 323 and the first switching valve 322, flows through one of the analytical columns 326 and 327, and flows into the detector 328. The detector 328 detects the sample fluid, and the detection result indicates whether the conjugate contained in the sample fluid meets the predefined standard. The detailed detection process is the same as that in FIG. 3, and thus will not be described. If the conjugate contained in the sample fluid does not meet the predefined standard, the first to sixth valves 161-166 are all switched to the closed state, and the seventh valve 523 and the eighth valve 524 are open. The fluid flowing out of the outlet main tube 137 flows into the circulating tube 51 and is temporarily stored in the recycling container 53. Later, the temporarily stored fluid flows through the eighth valve 524 under the control of the second delivery pump 172, flows into the inlet tube 131 and is re-conjugated in the flow reactor 10.

If the conjugate contained in the sample fluid sampled after re-conjugation meets the predefined standard, the sixth valve 166 is switched to the opened state, the seventh valve 523 is switched to the closed state, and the fluid flowing out of the outlet main tube 137 is collected into the fifth container 145. If the conjugate contained in the sample fluid sampled after re-conjugation still does not meet the predefined standard, the first to sixth valves 161-166 are maintained in the closed state, the seventh valve 523 and the eighth valve 524 are maintained in the opened state, and the re-conjugated fluid continues to flow into the circulating tube 51 to be re-conjugated until the produced conjugate meets the predefined standard. In the cyclic conjugation process, the fluid conducting the conjugation reaction in the flow reactor 10 is the fluid delivered by the circulating tube 51 until the fluid in the recycling container 53 and the circulating tube 51 is substantially discharged. The flow rate of the fluid may be determined by presetting the pump speed of the second delivery pump 172. The flow rate of cyclic conjugation is calculated by dividing a retention volume of the recycling container 53 (such as ⅓ of the reaction volume of the flow reactor 10) by the retention time according to different process requirements. When the fluid in the recycling container 53 and the circulating tube 51 is substantially discharged, the second valve 162, the third valve 163 and the fourth valve 164 are switched to the opened state, and the seventh valve 523 and the eighth valve 524 are switched to the closed state, so that the first reaction fluid in the second container 142 and the second reaction fluid in the third container 143 continuously flow into the flow reactor 10 to conduct the conjugation reaction. The conjugation process of the conjugation device 500 is the same as the conjugation process 400 of the conjugation device 300 in FIG. 3, and thus will not be described.

As described above, the conjugation conditions of the moieties contained in the reaction fluid can be monitored on line. By adding the circulating flow path in the conjugation device 500, when the detection result of the conjugate meets the standard, the fluid flowing out of the flow reactor is automatically collected, and when the detection result of the conjugate does not meet the standard, the fluid flowing out of the flow reactor is recycled into the flow reactor to be re-conjugated until the standard is met. The whole production process of the conjugate is automatically completed without manual sampling by the operator in the production process, thereby increasing the process convenience, decreasing the personnel operation complexity and avoiding possible human errors.

In addition, as shown in FIG. 5, in the present embodiment, a pressure sensing module 525 and a flow measuring module 526 are respectively arranged on the inlet main tube 131 of the conjugation flow path. Therefore, the fluid entering the inlet main tube 131 flows through the pressure sensing module 525 and the flow measuring module 526 and then enters the heating module 181. A pressure threshold may be set for the pressure sensing module 525 in advance, and when a fluid pressure measured by the pressure sensing module 525 exceeds the pressure threshold, the conjugation device 500 sends an alarm and automatically pauses to avoid burst of the flow reactor 10 due to an extremely high pressure. The flow measuring module 526 can monitor the flow of the fluid flowing through the inlet main tube 131 in real time.

In other embodiments, the pressure sensing module 525 and/or the flow measuring module 526 may also be arranged on the outlet main tube 137 to monitor the pressure and the flow of the fluid flowing out of the outlet 102 of the flow reactor 10 in real time. In addition, in other embodiments, other measuring devices, such as a conductivity metering module, a pH metering module and a UV detecting module, may be arranged on the inlet main tube 131 and/or the outlet main tube 137, so as to monitor parameters such as conductivity, pH and UV value of the conjugation buffer solution, the reaction fluids and/or the fluid flowing out of the outlet 102 of the flow reactor 10 in real time. In other embodiments, an automatic collector may be arranged on the outlet main tube 137, so as to collect the fluid flowing out of the outlet 102 of the flow reactor 10 in sections.

The above described first to sixth valves 161-166, the first delivery pump 171, the second delivery pump 172, the sampling pump 321, the first switching valve 322, the elution pump 323, the second switching valve 324 and the detector 328 are identical to those in the conjugation device 300 in FIG. 3. The control units or processing units of the various components are commutatively coupled to one computing device. The control units or the processing units of the pressure sensing module 525, the flow measuring module 526 and the seventh and eighth valves 523-524 are commutatively coupled to the same computing device, thereby enabling them to cooperate with each other. In addition to the above described content, in the present embodiment, the pressure sensing module 525 and the flow measuring module 526 transmit the measurement results to the control application in the computing device. The control application makes control decision based on these measurement results and transmits the control signals to the related components. The setup parameters in the control application may further include the pressure threshold, a flow threshold, the flow rate during cyclic conjugation, and the like. The view application in the computing device further displays real-time data of the above parameters received from the control application via the user interface.

In the above embodiments, the ligase is directionally immobilized onto the support and filled into the flow reactor, so that the two moieties of the conjugate to be produced contained in the reaction fluid are continuously and stably conjugated while the reaction fluid passes the fluid reactor. Compared with the chemical conjugation, the conjugation device greatly decreases the process steps, significantly reduces the complexity and is highly suitable to save expensive manufacturing costs. Moreover, by virtue of the flow reactor, linear scale-up of the conjugation process can be realized to satisfy industrial demands for larger scale s, unit time for conjugation, and the occupied space in the manufacturing area is reduced. By producing the bioconjugates using the conjugation device, site-specific conjugation between payload-linker and targeting molecule is realized, the homogeneity is improved, and accordingly the therapeutic window is widened. In addition, the conjugation process can be integrated with production procedures of biomolecules such as monoclonal antibodies. For example, conjugation may be completed at stages of producing monoclonal antibody intermediates and monoclonal antibody stock solutions. Therefore, the process is high in flexibility and excellent in coherence.

In still another embodiment of the disclosure, a method for producing a conjugate is provided. The method includes: providing at least one kind of reaction fluid containing a first moiety and a second moiety of a conjugate to be produced; and producing the conjugate by using any of the conjugation devices in the above embodiments.

The above descriptions are merely optional embodiments of the disclosure, rather than a limitation to the embodiments of the disclosure. For those skilled in the art, various modifications and changes can be made to the embodiments of the disclosure.

The scope of the claims conforms to the broadest interpretation, and thus, includes all the modifications and equivalent structures and functions. Any modifications, equivalences and improvements made within the spirit and principles of the embodiments of the disclosure shall be included in the protection scope of the claims of the disclosure.

What is claimed is:

1. A conjugation device, comprising:
   at least one flow reactor having an inlet and an outlet, each flow reactor being filled with a support, and a ligase is immobilized onto the support;
   a fluid delivery unit in fluid communication with the inlet of the at least one flow reactor and configured to continuously provide the at least one flow reactor with at least one kind of reaction fluid according to stages of a conjugation process, the at least one kind of reaction fluid including a first moiety and a second moiety of a conjugate to be produced; and
   a fluid collection unit in fluid communication with the outlet of the at least one flow reactor and configured to control collection of fluid flowing out of the outlet of the at least one flow reactor according to the stages of the conjugation process, wherein
   in a period of enabling the at least one kind of reaction fluid to continuously flow through the at least one flow reactor, a conjugation reaction is conducted between the first moiety and the second moiety under catalysis of the ligase to produce the conjugate.

2. The conjugation device according to claim 1, wherein the at least one kind of reaction fluid comprises first reaction fluid and second reaction fluid, the first reaction fluid containing the first moiety and the second reaction fluid containing the second moiety.

3. The conjugation device according to claim 2, wherein the conjugation process sequentially comprises the following stages: equilibrium prior to reaction, conjugation reaction, post-reaction, and flushing after post-reaction, and wherein the fluid delivery unit is further configured to:
   continuously provide the at least one flow reactor with a buffer solution during the stages of equilibrium prior to reaction, post-reaction and flushing after post-reaction; and
   continuously and simultaneously provide the at least one flow reactor with the first reaction fluid and the second reaction fluid during the stage of conjugation reaction.

4. The conjugation device according to claim 3, wherein the fluid delivery unit comprises a first delivery pump and a second delivery pump, a first container and a second container are respectively connected to the first delivery pump via a first container outlet tube and a second container outlet tube, a third container is connected to the second delivery pump via a third container outlet tube;
   the first delivery pump and the second delivery pump are respectively connected to an inlet main tube via a first inlet branch tube and a second inlet branch tube, and the inlet main tube is connected to the inlet of the at least one flow reactor;
   the fluid delivery unit further comprises a first valve, a second valve, a third valve and a fourth valve;
   the first valve, the second valve and the third valve are respectively arranged on the first container outlet tube, the second container outlet tube and the third container outlet tube and are respectively used for controlling flow path of fluid in the first container outlet tube, the second container outlet tube and the third container outlet tube; and
   the fourth valve is arranged on the first inlet branch tube and is used for controlling flow path of fluid in the first inlet branch tube.

5. The conjugation device according to claim 4, wherein
   during the stages of equilibrium prior to reaction, post-reaction and flushing after post-reaction, the first valve and the fourth valve are opened, while the second valve and the third valve are closed; and
   during the stage of conjugation reaction, the first valve is closed, while the second valve, the third valve and the fourth valve are opened.

6. The conjugation device according to claim 4, wherein
   the first container outlet tube, the second container outlet tube, the third container outlet tube, the first inlet branch tube, the second inlet branch tube and the inlet main tube are disposable or non-disposable and respectively made of one of stainless steel, titanium and silicone; and
   the first container, the second container and the third container are respectively selected from one of disposable liquid storage bags, disposable liquid storage bottles, stainless steel containers and both disposable and non-disposable glass or plastic containers.

7. The conjugation device according to claim 3, wherein the fluid collection unit is further configured to:
   collect fluid flowing out of the outlet of each flow reactor into a fourth container during the stages of equilibrium prior to reaction, and flushing after post-reaction; and
   collect fluid flowing out of the outlet of each flow reactor into a fifth container during the stages of conjugation reaction and post-reaction.

8. The conjugation device according to claim 7, wherein
   the fourth container and the fifth container are respectively connected to an outlet main tube via a fourth container inlet tube and a fifth container inlet tube, and the outlet main tube is connected to the outlet of the at least one flow reactor; and
   the fluid collection unit comprises a fifth valve and a sixth valve respectively arranged on the fourth container inlet tube and the fifth container inlet tube and used for controlling flow path of fluid in the fourth container inlet tube and the fifth container inlet tube.

9. The conjugation device according to claim 8, wherein
   during the stages of equilibrium prior to reaction and flushing after post-reaction, the fifth valve is opened, while the sixth valve is closed; and
   during the stages of conjugation reaction and post-reaction, the fifth valve is closed, while the sixth valve is opened.

10. The conjugation device according to claim 8, wherein the fourth container inlet tube, the fifth container inlet tube and the outlet main tube are disposable or non-disposable and respectively made of one of stainless steel, titanium and silicone; and the fourth container and the fifth container are respectively selected from one of disposable liquid storage bags, disposable liquid storage bottles, stainless steel containers, and both disposable and non-disposable glass or plastic containers.

11. The conjugation device according to claim 1, wherein the conjugation device further comprises:
a sampling detection unit in fluid communication with the outlet of the at least one flow reactor and configured to:
collect sample fluid from the fluid flowing out of the outlet of the at least one flow reactor according to preset sampling time; and
detect a conjugate in the sample fluid to obtain a detection result indicating whether the conjugate meets a predefined standard.

12. The conjugation device according to claim 11, wherein
the sampling detection unit comprises a sampling pump, a first switching valve, an elution pump, at least one analytical column and a detector, the sampling pump is connected to the outlet of the at least one flow reactor via a sampling tube, a sample loop is arranged on the first switching valve and the first switching valve is able to switch between a first state and a second state according to the preset sampling time; and wherein
when the first switching valve is in the first state, the sampling pump is in fluid communication with the sample loop, and configured to collect the sample fluid from the fluid flowing out of the outlet of the at least one flow reactor via the sampling tube and pump the sample fluid into the sample loop; and
when the first switching valve is in the second state, the elution pump, the sample loop, the at least one analytical column and the detector are in fluid communication via a detection tube, and the elution pump is configured to pump an eluant into the detection tube to enable the eluant to flow through the sample loop, thereby enabling the sample fluid in the sample loop to flow through one of the at least one analytical column before entering the detector.

13. The conjugation device according to claim 12 further comprising two analytical columns, wherein the sampling detection unit further comprises a second switching valve able to switch between two states and a washing pump; and
when the second switching valve is in any of the states, the sample loop and the detector are in fluid communication with one of the two analytical columns, the eluant enables the sample fluid in the sample loop to flow into the one analytical column, the washing pump is in fluid communication with the other analytical column and configured to pump buffer solution into the other analytical column for equilibrating.

14. The conjugation device according to claim 11, wherein the conjugation device further comprises a recycling unit arranged between the inlet and the outlet of the at least one flow reactor, wherein
when the detection result indicates that the conjugate does not reach the predefined standard, the fluid collection unit is to stop collection of the fluid flowing out of the outlet of the at least one flow reactor, and the recycling unit is to control the at least one fluid flowing out of the outlet of the at least one flow reactor to enter the inlet again so as to conduct a re-conjugation reaction in the at least one flow reactor.

15. The conjugation device according to claim 14, wherein the recycling unit comprises a seventh valve arranged on a recycling tube connected between the inlet and the outlet of the at least one flow reactor, and a recycling container is arranged on the recycling tube, wherein
when the detection result indicates that the conjugate does not meet the predefined standard, the seventh valve is opened, and the fluid flowing out of the outlet of the at least one flow reactor flows through the recycling tube and the recycling container and then flows into the inlet.

16. The conjugation device according to claim 1, wherein the at least one flow reactor is a conjugation column.

17. The conjugation device according to claim 1, wherein the first moiety comprises one of a recognition motif of ligase acceptor substrate and a recognition motif of ligase donor substrate, and the second moiety comprises the other of the recognition motif of ligase acceptor substrate and the recognition motif of ligase donor substrate.

18. A method for producing a conjugate, comprising:
providing at least one kind of reaction fluid containing a first moiety and a second moiety of a conjugate to be produced; and
producing the conjugate by using the conjugation device of claim 1.

19. A conjugation device, comprising:
at least one flow reactor having an inlet and an outlet, each flow reactor being filled with a support, and a ligase is immobilized onto the support;
a fluid delivery unit in fluid communication with the inlet of the at least one flow reactor and configured to continuously provide the at least one flow reactor with at least one kind of reaction fluid according to stages of a conjugation process, the at least one kind of reaction fluid including a first moiety and a second moiety of a conjugate to be produced; and
a fluid collection unit in fluid communication with the outlet of the at least one flow reactor and configured to control collection of fluid flowing out of the outlet of the at least one flow reactor according to the stages of the conjugation process, wherein
in a period of enabling the at least one kind of reaction fluid to continuously flow through the at least one flow reactor, a conjugation reaction is conducted between the first moiety and the second moiety under catalysis of the ligase to produce the conjugate, and
wherein the ligase is a sortase.

* * * * *